United States Patent [19]

Trimnell et al.

[11] 4,439,488

[45] Mar. 27, 1984

[54] ENCAPSULATION BY ENTRAPMENT WITHIN POLYHYDROXY POLYMER BORATES

[75] Inventors: Donald Trimnell; Baruch S. Shasha, both of Peoria, Ill.

[73] Assignee: The United States of America as represented by the Secretary of Agriculture, Washington, D.C.

[21] Appl. No.: 352,662

[22] Filed: Feb. 26, 1982

[51] Int. Cl.³ .................... B01J 13/02; B32B 23/12; B32B 27/04
[52] U.S. Cl. .................... 428/402.24; 71/64.11; 71/DIG. 1; 252/522 A; 264/4.1; 264/4.3; 424/22; 424/33; 424/35; 426/96; 426/103; 427/213.3; 427/213.31; 427/213.36; 428/402.2; 428/402.21; 428/402.22
[58] Field of Search ............ 252/316, 522 A; 424/22, 424/33, 35; 71/64.11, DIG. 1; 426/96, 103; 427/213.3, 213.31, 213.36; 428/402.2, 402.21, 402.22, 402.24; 264/4.1, 4.3

[56] References Cited

U.S. PATENT DOCUMENTS

| | | | |
|---|---|---|---|
| 3,137,630 | 6/1964 | Hecker et al. | 264/14 |
| 3,323,922 | 6/1967 | Durst | 426/89 |
| 3,875,074 | 4/1975 | Vassiliades et al. | 252/316 |
| 4,277,364 | 7/1981 | Shasha et al. | 252/316 |

FOREIGN PATENT DOCUMENTS

1222016 2/1971 United Kingdom ............. 252/316

OTHER PUBLICATIONS

H. Deuel et al., Nature 161: 96–97, (1948), "Reaction of Boric Acid with Polysaccharides".
J. Hollo et al., Fette, Seifen, Anstrichmittel 59: 94–98, (1957), "Undersuchung der Jod-Reaktion von Stärke".
R. F. Nickerson, J. Appl. Polym. Sci. 15: 111–116, (1971), "Thickening of Poly(Vinyl Alcohol) by Borate".
E. P. Czerwin, Chem. Abstr. 87: 25086s, (1977), "Poly(-Vinyl Alcohol)-Starch Composition".

*Primary Examiner*—Richard D. Lovering
*Attorney, Agent, or Firm*—M. Howard Silverstein; David G. McConnell; Curtis P. Ribando

[57] ABSTRACT

Chemical biological agents to be encapsulated are dissolved or dispersed in an aqueous paste of a gel-forming polyhydroxy polymer. Subsequent addition of boric acid or a boric acid derivative at an alkaline pH converts the paste into a gel, thereby entrapping the agents in a protective matrix. Encapsulation of biologically active compositions provides a shield against hostile environments, improves safety in handling, and slows the release of such compounds to the surrounding medium. Highly volatile liquids are protected against losses by evaporation. Encapsulation also provides protection against decomposition from exposure to ultraviolet light.

15 Claims, No Drawings

ENCAPSULATION BY ENTRAPMENT WITHIN POLYHYDROXY POLYMER BORATES

BACKGROUND OF THE INVENTION

1. Field of the Invention

Although the United States attempts to control pests such as weeds, insects, nematodes, and fungi with about 2 billion pounds of pesticides per year, these pests are still responsible for annual farm production losses of 35 billion dollars. This loss is equivalent to 30% of the total market value of farm products. Part of the problem involves a lack of full availability of the pesticide to the target as a result of wind, evaporation, leaching, degradation, and waste on nontargeted areas. One way of achieving more efficient pesticide usage is through controlled release formations capable of reducing rates of application, allowing fewer applications, limiting control to targeted areas, reducing evaporative and degradative losses, and providing a slow release of pesticide concurrent with the presence of moisture and soil microorganisms. In addition, controlled release provides for a safer environment, reduces toxicity to desirable plants, makes pesticides safer to handle, and extends residual life of pesticides without carryover into the subsequent growing season.

This invention relates to a novel method of encapsulating pesticides and other chemical biological agents for controlling their release and to the compositions prepared thereby.

2. Description of the Prior Art

Various approaches to the controlled release of chemical biological agents by means of a starch-based encapsulating material have previously been disclosed. In U.S. Pat. Nos. 4,277,364 and 4,344,857 Shasha et al. disclose methods of encapsulation whereby a polyhydroxy polymer xanthate and a coupling agent are reacted from a single phase to form an insolubilized xanthide matrix, thereby entrapping the active agent. The Shasha et al. system has the advantage of operating in both aqueous and nonaqueous two-phase systems, as well as in single-phase systems in which the matrix-forming materials and the core material are soluble in the same solvent. Another advantage is that the entire reaction mixture is converted into a solidified mass which is readily dried and ground into a usable product after pressing out excess water. This obviates the recovery from a liquid medium as necessitated by most coacervation and interfacial polymerization methods. However, widespread commercial acceptance of the Shasha et al. methods has been hindered by the reluctance of the industry to handle carbon disulfide which is both flammable and toxic.

In U.S. patent application Ser. No. 202,396, filed Oct. 30, 1980, now U.S. Pat. No. 4,382,813, Shasha discloses a system for encapsulating certain types of pesticidal agents by the rapid insolubilization of a starch-containing material alkoxide with a bivalent cation selected from the group of calcium, barium, and strontium. While this system is applicable to water-insoluble agents, it is not particularly suitable for those which are water-soluble, nor for substances susceptible to alkali degradation.

SUMMARY OF THE INVENTION

We have now surprisingly discovered a method of encapsulating virtually all types of chemical biological agents regardless of solubility characteristics. The agents are dissolved or dispersed in an aqueous polyhydroxy polymer (PHP) paste, which is reacted at an alkaline pH with boric acid or a boric acid derivative to form a continuous insolubilized matrix gel entrapping discontinuous domains of the agent. This system not only avoids the use of xanthates, but also is operative under mildly alkaline pH's thereby permitting encapsulation of acid-sensitive and most alkali-sensitive chemicals. Moreover, by employing solids contents far in excess of those permissible with the bivalent cation adduct system of Shasha, supra, dehydration of the final product is facilitated.

In accordance with this discovery, it is an object of the invention to provide a facile, universal, and industrially acceptable method for encapsulating chemical biological agents.

It is also an object of the invention that the primary matrix-forming material be derived from either natural renewable resources or from inexpensive synthetic sources.

It is a further object of the invention to provide a novel free-flowing particulate product in which discontinuous domains of biologically active core material are entrapped by a continuous matrix of gelled PHP.

Another object of the invention is to provide a product in which the encapsulated substance is sufficiently protected to be safe for handling, controllably released to the environment, and resistant to losses by volatilization, leaching, wind transport, and sunlight decomposition.

Other objects and advantages of this invention will become readily apparent from the ensuing description.

DETAILED DESCRIPTION OF THE INVENTION

The polyhydroxy polymers (PHP), suitable as matrix-forming materials in accordance with the invention, include any such polymers which are capable of forming a gel. Included are the natural starches such as cereal and potato starch, and flours containing the same, as well as derivatized and modified starches as known in the art. These starches may be in their original granular form or else they may be partially or completely pregelatinized. Illustrative of other gellable PHP are carboxymethylcellulose (CMC), dextran, xylan, and polyvinyl alcohol.

The PHP are prepared for the encapsulation reaction by conversion into an aqueous paste. Pasting of pregelatinized starch is of course readily accomplished by stirring the material into water. The other PHP's are pasted either by heating a dispersion thereof in water or by conversion to an alkoxide with an alkali metal hydroxide. Sodium and potassium hydroxides are the most suitable reagents for alkoxidation and will react with PHP's in aqueous suspension at ambient temperature. The ratio of alkali metal:repeating polymer unit employed for this step should be in the range of 1:4 to 1:1, and preferably between 1:3 and 1:2. Levels of alkali greater than 1:1 cause unnecessary occlusion of borate salt in the final product. For purposes of this invention, the PHP in paste form is considered to be in the aqueous phase which will constitute the continuous phase of the encapsulation system.

The concentration of the PHP in the aqueous suspension prior to pasting should be maintained within the range of about 10-40% solids, and preferably between about 25 and 35% solids. At the higher concentrations, recovery of the final product is facilitated as described in further detail below.

The core material to be encapsulated is mixed with the PHP either prior to or subsequent to pasting by any conventional means of obtaining a relatively uniform distribution. At the higher PHP solids concentrations, incorporation prior to pasting is preferable. The domains of agent which constitute the discontinuous phase of the dispersion should be sufficiently small so as to render the dispersion stable until the paste is insolubilized. It would be within the skill of a person in the art to determine the maximum level at which a particular agent can be effectively loaded into the system. For nearly complete encapsulation, the ratio of agent:PHP on a dry weight basis will typically be in the range of 1:10 to 2:3, though with some agents it may be as high as 1:1. For purposes of performance, effective amounts of core materials depend entirely on the type and characteristics of the core material, on matrix thickness, and on the intended utility of the product. A very volatile liquid, for instance, would require a thicker structure than a nonvolatile solid, and accordingly should be incorporated at a lower level. Similarly, a volatile liquid to be completely withheld from the environment would be incorporated at a lower level than one to be used as a slow-release pesticide. "An effective amount of a suitable biological agent" is defined herein as that amount of core material which will achieve the desired result (e.g., attract, repel, or kill pests, release a detectable aroma or flavor, or enhance the growth of plants) when the encapsulated composition containing the effective amount of the agent is placed in the proper environment.

Chemical biological agents which are suitable for use herein may be any organic or inorganic solids capable of being finely divided or any liquid, provided that the agent does not interfere with the encapsulating process, and does not react with or dissolve the encapsulating matrix. Particularly envisioned are chemicals and chemical formulations which meet the above criteria and which are classified as a known herbicide, insecticide, fungicide, nematocide, bactericide, rodenticide, molluscicide, acaricide, larvacide, fumigant, animal repellant, insect repellant, plant growth regulator, fertilizer, pheromone, sex lure, flavor composition, or odor composition.

Exemplary herbicides include S-ethyl dipropylcarbamothioate, S-propyl dipropylcarbamothioate, S-propyl butylethylcarbamothioate, S-ethyl cyclohexylethylcarbamothioate, S-ethyl bis(2-methylpropyl)carbamothioate, S-ethyl hexahydro-1-H-azepine-1-carbothioate, S-(2,3,3-trichloro-2-propenyl)-bis(1-methylethyl)carbamothioate, 2,6-dinitro-N,N-dipropyl-4-(trifluoromethyl) benzenamine, N-butyl-N-ethyl-2,6-dinitro-4-(trifluoromethyl) benzenamine, N-(cyclopropylmethyl)-2,6-dinitro-N-propyl-4-(trifluoromethyl) benzenamine, N-ethyl N-(2-methyl-2-propenyl-2,6-dinitro-4-(trifluoromethyl) benzenamine, dimethyl 2,3,5,6-tetrachloro-1,4-benzenedicarboxylate, N-(1,1-dimethylethyl)-N'-ethyl-6-methylthio)-1,3,5-triazine-2,4-diamine, 2-chloro-N-(2-ethyl-6-methylphenyl)-N-(2-methoxy-1-methylethyl) acetamide, 2-chloro-N-(2,6-diethylphenyl)-N-(methoxymethyl) acetamide, the polypropylene glycol butyl ether ester of 2,4-dichlorophenoxyacetic acid, and 2,6-dichlorobenzonitrile.

Exemplary fungicides include 3a,4,7,7a-tetrahydro-2-[(trichloromethyl)thio]-1-H-isoindole-1,3(2H)-dione, 3a,4,7,7a-tetrahydro-2-[(1,1,2,2-tetrachloroethyl)thio]-1-H-isoindole-1,3(2H)-dione, 2,4,5,6-tetrachloro-1,3-benzenedicarbonitrile, and sodium methyldithiocarbamate.

Exemplary insecticides include N-[[(4-chlorophenyl)amino]carbonyl]-2,6-difluorobenzamide, 1,1'-(2,2,2-trichloroethylidene) bis(4-chlorobenzene), 2,2-dimethyl-1,3-benzodioxol-4-yl methylcarbamate, O,O-diethyl O-6-methyl-2-(1-methylethyl)-4-pyrimidinyl phosphorothioate, and O-ethyl-S-phenyl ethylphosphonodithioate. 1,2-dibromo-3-chloropropane is illustrative of a suitable nematocide. Other compositions suitable as core materials for use in accordance with the invention such as organic and inorganic fertilizers, adjuvants, and the like, will be known to those skilled in the art. Core materials dissolved, emulsified, or otherwise dispersed in solvents or carriers, as well as compatible combinations of the above types of compositions are also easily encapsulated by the instant method.

For the PHP paste to gel, it must be at an alkaline pH, which for purposes of the invention is defined as being greater than about 7.5. If the material were pasted by treatment with a strong hydroxide as previously discussed, the pH will typically be on the order of about 9–11, depending upon the PHP and the biological agent. If, on the other hand, the pasting were effected by heating, the pH can be adjusted by addition of alkali. For agents sensitive to strongly alkaline conditions, it is recommended that the pH be adjusted to within the range of about 7.5 to 8.5 by means of ammonium hydroxide. Alkali-sensitive agents are also advantageously protected by deferring the adjustment until just prior to or simultaneously with the gelling reaction.

The paste is gelled in the presence of the biological agent by the addition of a gelling agent selected from the group of boric acid and boric acid derivatives. Boric acid is usually preferred where it is desirable to partially or completely neutralize the paste, particularly if it is strongly basic. Otherwise, suitable derivatives include any of the borates such as sodium metaborate, sodium tetraborate (borax), and ammonium pentaborate. The gelling agent may either be predissolved in an aqueous medium or else added as a finely pulverized powder having a particle size of less than about 60 mesh. Its level should be selected to cause sufficient gelation without excessive salt occlusion. Generally, the molar ratio of gelling agent:hydroxide will range between 1:5 and 5:1, and preferably between 1:2 and 2:1. It is preferred to rapidly mix the gelling agent with the paste in order to effect an essentially instantaneous reaction. Upon entering into solution the agent reacts with the PHP from a single phase. The temperature is not particularly critical, with gelling readily occurring at ambient conditions. The result is a substantially homogeneous rubbery mass analogous to the precursive dispersion in which, now, discontinuous domains of active ingredient are uniformly dispersed throughout a continuous, insolubilized matrix gel.

The recovery procedure is aimed at converting the rubbery mass to discrete, free-flowing, nonagglomerating particles. In accordance with one method of recovery contemplated herein, the matrix gel is admixed with a powdery coating material in a coating:PHP ratio in the range of about 1:10 to about 1:1 on a dry weight basis. By subjecting the gel to shear during the mixing, it is simultaneously broken into small particles and coated to prevent reagglomeration. The level of coating material together with the type and extent of shearing will determine the ultimate particle size. A preferred coating material is ungelatinized pearl corn starch, though other powdery materials such as flours, silicas, clays, and the like as known in the art can advantageously be used. In an alternate embodiment, the gel may be broken into small particles and then dehydrated by suspension in an excess of alcohol. Water diffuses from the matrix into the alcohol, with minimal loss of active ingredient. While both methods yield nonagglomerating particles which can be readily sieved and air dried, the coating method is preferred for maximizing the retention of volatile agents. It is believed that the coating material seals the open pores near the particle surface, and that as a rule, there is a direct relationship between the level of addition and the percent volatiles retained. It can be appreciated by the skilled artisan that by proper selection of materials and proportions within the scope of the invention as described above, nearly quantitative encapsulation of chemical biological agents is attainable, and the release characteristics of the products can be tailored to exacting specifications.

After the product has dried to yield a friable granular or powdered material, rewetting initiates biodegradation of the matrix and release of the active ingredient. Fields, gardens, and the like in which pesticides, attractants, repellants, plant growth regulators, and fertilizers are normally used contain sufficient natural or added moisture to initiate release. While not desiring to be bound to any particular theory, it is believed that the mechanism of release is effected to the biodegradation of the polyhydroxy polymer matrix as well as by displacement by water and diffusion through imperfections in the matrix.

The following examples are intended only to further illustrate the invention and are not intended to limit the scope of the invention which is defined by the claims.

EXAMPLE 1

Forty-five grams of granular pearl corn starch was slurried with 70 ml. of water and 20 g. of "Eradicane 6.7E" [S-ethyl dipropylthiocarbamate (EPTC) emulsifiable concentrate (e.c.), 83% active ingredient (a.i.)]. A solution of 50 ml. of aqueous NaOH (3.3 g NaOH) was mixed into the slurry with a "Waring" type blender in order to paste the starch. The addition of 5 g. of finely pulverized boric acid was blended into the paste, rapidly converting it into a rubbery gel. The blending was continued during the addition of 18 g. ungelatinized pearl corn starch as a coating agent to give nonadherent particles passing 8 mesh. The yield after drying was 88.3 g. with 89% of the particles in the 10–35 mesh range. The product contained 1.43% N, corresponding to 19.3% active ingredient and 97% recovery. The percent recovery represents the percent of the added active ingredient found in the final product.

EXAMPLE 2

Forty-five grams of sodium carboxymethylcellulose was mixed with 70 ml. of water and 10 g. of "Eradicane 6.7E." The mixture was warmed to 50° C. and stirred to obtain a uniform paste. A solution of 50 ml. of aqueous NaOH (3.3 g NaOH) was mixed into the paste with a "Waring" type blender followed by the addition of 5 g. of finely pulverized boric acid. The resultant rubbery gel was mixed with 30 g. of ungelatinized pearl corn starch to give nonadherent particles passing 8 mesh. The yield after drying overnight was 93.7 g. and contained 0.62% N, corresponding to 8.4% active ingredient and 94% recovery.

EXAMPLE 3

Fifteen grams of pharmaceutical dextran, M.W. 68,000, was pasted in a mixture of 10 ml. of aqueous NaOH (0.67 g. NaOH) and 7 ml. of water. Three grams of "Eradicane 6.7E" followed by 1 g. of finely pulverized boric acid were added, and the mixture was blended until gelatin ensued. The product was coated with 6 g. of ungelatinized pearl corn starch to given nonadherent particles passing 8 mesh. The yield after drying overnight was 25.3 g. and contained 0.63% N, corresponding to 8.5% active ingredient and 86% recovery.

EXAMPLE 4

Fifteen grams of wheat xylan was mixed with 3 g. of "Eradicane 6.7E," 25 ml. of water, and 17 ml. of aqueous NaOH (1.1 g. NaOH). The resulting paste was mixed with 2 g. of finely pulverized boric acid to form a gel. The gel was coated with 10 g. of ungelatinized pearl corn starch in a blender and sieved to pass 8 mesh. The yield after drying overnight was 30.8 g. and contained 0.42% N, corresponding to 5.7% active ingredient and 70% recovery.

EXAMPLE 5

Fifteen grams of polyvinyl alcohol ("T-25," DuPont) was suspended in 85 ml. of water and warmed to 60° C. to dissolve. After cooling to 20° C., 10.1 g. of "Fumazone" [1,2-dibromo-3-chloropropane (DBCP), e.c., 86% a.i.] was mixed in followed by the addition of 25 ml. aqueous NaOH (1.67 g. of NaOH). Three grams of finely pulverized boric acid induced gelation. The product was coated with 5 g. of ungelatinized pearl corn starch and sieved to pass 4 mesh. The yield after drying overnight was 31.7 g. with 77% of the particles in the 4–10 mesh range. The product contained 17.9% halogen corresponding to 21.6% active ingredient and 75% recovery.

EXAMPLE 6

Forty-five grams of acid-modified starch ("Clinton 290B") was slurried with 45 g. of water and 10 g. of "Sutan Plus 6.7E" [S-ethyl di-isobutylthiocarbamate (butylate), e.c., 85% a.i.]. The paste was converted to a rubbery gel by blending with 5 g. of finely pulverized boric acid. The product was coated with 28 g. of ungelatinized pearl corn starch, and the particles sieved to pass 10 mesh. The yield after drying overnight was 86.5 g. and contained 0.60% N, corresponding to 9.3% active ingredient and 94% recovery.

EXAMPLE 7

Forty-five grams of ungelatinized pearl corn starch was slurried with 70 ml. of water and 10 g. of urea was dissolved in the slurry. The slurry was then pasted with 50 ml. of aqueous NaOH (3.3 g. NaOH) and the paste was converted to a rubbery gel by blending with 5 g. of finely pulverized boric acid. Five grams of pearl corn starch was added and the particles sieved to pass 8 mesh. The yield after air drying overnight was 64.1 g. and contained 6.82% N, corresponding to 14.6% active ingredient and 100% recovery.

EXAMPLE 8

Forty-five grams of ungelatinized pearl corn starch was slurried with 30.5 g. of "Vapam" (32.7% aqueous sodium methyldithiocarbamate) and 40 ml. of water.

The slurry was pasted with 50 ml. of aqueous NaOH (3.3 g. of NaOH) and the paste was converted to a rubbery gel by the addition of 5 g. of finely pulverized boric acid. The product was coated with 5 g. of pearl corn starch, enabling the particles to be sieved to pass 8 mesh. The yield after drying was 67.0 g. and contained 6.6% S, corresponding to 13.3% active ingredient and 89% recovery.

EXAMPLE 9

Forty-five grams of ungelatinized pearl corn starch was slurried with 70 ml. of water and 10.1 g. of powdered "Treflan" (98.6% trifluralin). A solution of 50 ml. of aqueous NaOH (3.3 g. of NaOH) was added and mixed rapidly in the blender until the temperature rose to 50° C. to cause the "Treflan" to melt and disperse well into the paste. Five grams of finely pulverized boric acid was mixed in until gelation was complete. The product was coated with 6 g. of pearl corn starch and sieved to pass 8 mesh. The yield after drying overnight was 67.1 g. and contained 1.49% N, corresponding to 13.5% active ingredient and 91% recovery. A sample washed with hexane showed that 98% of the a.i. was encapsulated and only 2% was on the surface.

EXAMPLE 10

Forty-five grams of ungelatinized pearl corn starch was slurried with 70 ml. of water and 10.3 g. of technical "Sutan" (97.5% butylate). The slurry was pasted with 50 ml. of aqueous NaOH (3.3 g. NaOH), and gelled with 5 g. of boric acid. The gel was coated with 5 g. of additional pearl corn starch and sieved to pass 8 mesh. The yield after drying overnight was 65.7 g. and contained 0.84% N, corresponding to 13.1% active ingredient and 86% recovery.

EXAMPLE 11

Forty-five grams of ungelatinized pearl corn starch was slurried with 70 ml. of water and 13.3 g. of "Dacthal 75W" [2,3,5,6-tetrachloroterephthalic acid (chlorthal-dimethyl), wettable powder, 75% a.i.] was added. The slurry was pasted with 50 ml. of aqueous NaOH (3.3 g of NaOH) and gelled with 5 g. of boric acid. The gel was coated with 6 g. of additional pearl corn starch and sieved to pass 8 mesh. The yield after drying overnight was 71.7 g. and contained 6.3% Cl, corresponding to 14.5% active ingredient and 100% recovery.

EXAMPLE 12

Fifteen grams of polyvinyl alcohol ("T-25," DuPont) was suspended in 85 ml. of water and warmed to 60° C. to dissolve. After cooling to 20° C., 10 g. of "Eradicane 6.7E" was added and the mixture was gelled with 3 g. of ammonium pentaborate. Particles were coated with 10 g. of pearl corn starch and sieved to pass 8 mesh. The yield after drying overnight was 36.1 g. with 95% of the particles in the 10–35 mesh range. The product contained 3.70% S, corresponding to 21.9% active ingredient and 91% recovery.

EXAMPLE 13

A mixture of 0.150 g. of polyvinyl alcohol ("T-25," DuPont) in 0.85 ml. of water was warmed on the steam bath to dissolve the polyvinyl alcohol. Subsequently 0.100 g. of "Ficam" [2,2-dimethyl-1,3-benzodioxol-4-yl methylcarbamate (bendiocarb)] was blended in followed by 0.030 g. of sodium tetraborate (borax) to cause gelation. The product was coated with 0.100 g. of pearl corn starch and sieved to pass 8 mesh. The yield after drying overnight was 0.374 g. and contained 1.58% N, corresponding to 25.1% active ingredient and 94% recovery.

EXAMPLE 14

Forty-five grams of ungelatinized pearl corn starch was slurried with 70 ml. of water and 11.9 g. of "Eradicane 6.7E." The slurry was pasted with 50 ml. of aqueous NaOH (3.3 g. of NaOH) and was then converted to a rubbery gel with 5 g. of boric acid. The gel was broken manually into small pieces and suspended 30 minutes in 200 ml. of ethyl alcohol to yield a dehydrated product which was filtered and pulverized in a blender to pass 8 mesh. The yield after drying overnight was 63.3 g. with 96% of the particles in the 10–35 mesh range. The product contained 0.97% N, corresponding to 13.1% active ingredient and 83% recovery.

EXAMPLE 15

Forty-five grams of ungelatinized pearl corn starch was slurried with 70 ml. of water and 20 g. of "Vernam 7.0E" [S-propyl dipropylthiocarbamate (vernolate), e.c., 88% a.i.]. The slurry was pasted with 50 ml. of aqueous NaOH (3.3 g. of NaOH), and the paste was then converted to a rubbery gel with 5 g. of boric acid. The gel was mixed with 6 g. of "Hy-cel" silica to give nonadherent particles passing 8 mesh. The yield after drying overnight was 77.2 g. with 91% of the particles in the 10–35 mesh range. The product contained 1.27% N, corresponding to 18.4% active ingredient and 86% recovery.

EXAMPLE 16

Example 1 was repeated except that 6 g. instead of 18 g. of pearl corn starch was used to coat the product prior to drying. The yield after drying overnight was 78.0 g. with 72% of the particles in the 10–35 mesh range. The product contained 1.35% N, corresponding to 18.2% active ingredient and 84% recovery.

Samples of 0.100 g. in this mesh range was suspended in 1, 3, 5, and 7 ml. of water and evaporated to dryness overnight to demonstrate controlled release. Nitrogen analyses indicated that 20, 41, 48, and 64% of active ingredient was lost, respectively. Samples of 0.100 g. of the clay-formulated, commercial granular "Eptam 10G" (EPTC) were similarly evaporated with these quantities of water for comparison. In each instance a uniform 86% of the active ingredient was lost.

EXAMPLE 17

Forty-five grams of ungelatinized pearl corn starch was slurried with 40 ml. of water and 20 g. of "Eradicane 6.7E." The slurry was pasted with 40 ml. of aqueous NaOH (2.67 g. of NaOH) and 5 g. of boric acid was then added. After mixing for 10 minutes, a uniform gel was obtained. The gel was pulverized to pass 8 mesh and particles were sufficiently nonadherent for drying without addition of more starch. The yield after drying overnight was 65.0 g. and contained 1.45% N, corresponding to 19.6% active ingredient and 75% recovery. Upon storage for 3 days, the yield was 63.9 g. and contained 1.32% N, corresponding to 17.8% active ingredient and 67% recovery; thereafter the change was insignificant.

EXAMPLE 18

Forty-five grams of ungelatinized pearl corn starch was slurried with 250 ml. of water and 30 g. of "Eradicane 6.7E." The slurry was pasted with 75 ml. of aqueous NaOH (5 g. of NaOH) and the paste was converted to a rubbery gel with 5 g. of boric acid. The gel was divided manually into small pieces and dehydrated with two 200-ml. portions of ethyl alcohol over 30 minutes. The resulting alcohol-water solution was decanted and the remaining particles filtered and pulverized in a blender to pass 8 mesh. The yield after drying overnight was 62.0 g. with 94% of the particles in the 10-35 mesh range. The product contained 1.02% N, corresponding to 13.8% active ingredient and 33% recovery.

EXAMPLE 19

Forty-five grams of ungelatinized pearl corn starch was slurried with 70 ml. of water and pasted with 50 ml. of aqueous NaOH (3.3 g. of NaOH). Twenty grams of "Sutan Plus 6.7E" followed by 5 g. of boric acid were added and the paste was blended until a rubbery gel formed. Addition of 6 g. of pearl corn starch produced nonadherent particles which were sieved to pass 8 mesh. The yield after drying overnight was 74.9 g. and contained 1.38% N, corresponding to 21.6% active ingredient and 95% recovery.

EXAMPLE 20

Forty-five grams of pearl corn starch was slurried with 70 ml. of water and 20 g. of "Sutan Plus 6.7E." The slurry was pasted with 50 ml. of aqueous KOH (8.2 g. of KOH), and the paste was converted to a rubbery gel with 5 g. of boric acid. The gel was mixed with 18 g. of additional pearl corn starch to give nonadherent particles passing 8 mesh. The yield after drying overnight was 90.1 g. with 94% of the particles in the 10-35 mesh range. The product contained 1.08% N, corresponding to 16.7% active ingredient and 86% recovery.

EXAMPLES 21-33

A series of compounds was encapsulated by the following general procedure: 45 g. of ungelatinized pearl corn starch was slurried with 70 ml. of water and enough chemical biological agent to give 10 g. of active ingredient. The slurry was pasted with 50 ml. of aqueous NaOH (3.3 g. of NaOH) and then converted to a rubbery gel by blending with 5 g. of boric acid. The gel was mixed with 6 g. of additional pearl corn starch to give particles passing 8 mesh. Table I, below, lists compounds encapsulated and percent recovery of the active ingredient used for the encapsulation.

TABLE I

| Example | Agent encapsulated | % Recovery |
| --- | --- | --- |
| 21 | S—propyl dipropylcarbamothioate | 94 |
| 22 | S—propyl butylethylcarbamothioate | 96 |
| 23 | S—ethyl cyclohexylethyl carbamothioate | 95 |
| 24 | S—ethyl hexahydro-1-H—azepine-1-carbothioate | 84 |
| 25 | S—(2,3,3-trichloro-2-propenyl)-bis(1-methylethyl) carbamothioate | 95 |
| 26 | N—butyl-N—ethyl-2,6-dinitro-4-(trifluoromethyl) benzenamine | 100 |
| 27 | N—ethyl-N—(2-methyl-2-propenyl)-2,6-dinitro-4-(trifluoromethyl) benzenamine | 100 |
| 28 | N—(1,1-dimethylethyl)N'—ethyl-6-(methylthio)-1,3,5-triazine-2,4-diamine | 98 |
| 29 | 2,4-dichlorophenoxyacetic acid, propylene glycol butyl ether ester | 94 |
| 30 | 2,3,5,6-tetrachloro-1,3-benzenedicarbonitrile | 100 |
| 31 | O—ethyl-S—phenyl ethylphosphonodithioate | 81 |
| 32 | O,O—diethyl-O—6-methyl-2-(1-methylethyl)-4-pyrimidinyl phosphorothioate | 96 |
| 33 | 1,2-dibromo-3-chloropropane | 32 |

EXAMPLE 34

Forty-five grams of pregelatinized wheat starch was dispersed in a "Waring" blender with 120 ml. of water until a smooth paste formed. The paste was cooled to 25° C. and 10 g. of "Eradicane 6.7E" was mixed followed by 15.7 g. of sodium tetraborate (borax) to cause gelation. The product was coated with 18 g. of pearl corn starch and sieved to pass 8 mesh. The yield after drying overnight was 85.1 g. with 91% of the particles in the 10-35 mesh range. The product contained 0.66% N, corresponding to 8.9% active ingredient and 84% recovery.

EXAMPLE 35

Example 34 was repeated except that 11.4 g. of sodium metaborate was used instead of sodium tetraborate. Yield after drying overnight was 78.0 g. with 83% of the particles in the 10-35 mesh range. The product contained 0.78% N, corresponding to 10.5% active ingredient and 90% recovery.

EXAMPLE 36

Forty-five grams of ungelatinized pearl corn starch was slurried with 325 ml. of water and 10 g. of "Eradicane 6.7E." The slurry was pasted with 75 ml. of aqueous NaOH (5.0 g. of NaOH), and the paste was converted to a rubbery gel with 7.8 g. of boric acid. The gel was mixed manually with 18 g. of pearl corn starch, then broken into small pieces and air dried overnight. The dried particles were pulverized to cause reduction to the 10-35 mesh range. The yield was 84.7 g. with 89% of the particles in this range. The product contained 0.66% N, corresponding to 8.9% active ingredient and 88% recovery.

EXAMPLE 37

Twenty grams of pregelatinized corn flour was mixed with 100 ml. of water containing 4 ml. of ammonium hydroxide solution (29% ammonia) until a thick paste formed. Twenty grams of "Eradicane 6.7E" was blended into the paste followed by 30 g. of additional pregelatinized corn flour and then 2 g. of boric acid. A rubbery gel formed which was mixed with two 10-g.

portions of pregelatinized corn flour. The yield after drying overnight was 86.3 g. with 78% of the particles in the 12-35 mesh range. The product contained 2.63% S, corresponding to 15.6% active ingredient and 80% recovery. A water suspension of the product (5 g./40 ml.) showed pH 8.2.

EXAMPLE 38

Twenty grams of pregelatinized corn starch was mixed with 100 ml. of water containing 4 ml. of ammonium hydroxide solution (29% ammonia) until a thick paste formed. Twenty grams of "Eradicane 6.7E" was blended into the paste followed by 30 g. of additional pregelatinized corn starch and then 2 g. of boric acid. A rubbery gel formed which was mixed with two 10-g. portions of ungelatinized pearl corn starch to give particles passing 8 mesh. The yield after drying overnight was 85.1 g. with 74% of the particles in the 12-35 mesh range. The product contained 2.67% S, corresponding to 15.8% active ingredient and 80% recovery. A water suspension of the product (5 g./40 ml.) showed pH 8.2.

EXAMPLE 39

Fifty grams of pregelatinized corn starch was mixed with 100 ml. of water and mixed rapidly in the "Waring" blender until a smooth paste formed. Then 20 g. of "Eradicane 6.7E" and 2 g. of boric acid were blended into the paste. When well mixed, 4 ml. of ammonium hydroxide was added to form a rubbery gel. The gel was coated with 20 g. of pearl corn starch, pulverized, and sieved to pass 8 mesh. The yield after drying overnight was 86.1 g. The product contained 2.56% S, corresponding to 15.1% active ingredient and 78% recovery.

EXAMPLE 40

"Sutan Plus 6.7E" (85% a.i. butylate) containing the water-soluble crop protectant (safener) R-25788 (N,N-diallyl dichloroacetamide) was encapsulated as in Example 19 and compared with the same material encapsulated by the xanthide (Shasha et al., U.S. Pat. No. 4,277,364) and calcium adduct (Shasha, Ser. No. 202,396, now U.S. Pat. No. 4,382,813) methods as to butylate recovery and retention of safener in the product of each procedure.

Xanthide encapsulation: starch xanthate was prepared by mixing 45 g. of pearl corn starch with 250 ml. of water, gelatinizing the mixture with a solution of 5 g. of sodium hydroxide in 75 ml. of water, mixing the resulting paste with 5 ml. of carbon disulfide and allowed the paste to remain 1 hour at room temperature. Twenty grams of "Sutan Plus 6.7E" was dispersed using a "Waring" blender. A solution of 6.25 g. of concentrated sulfuric acid and 6.25 g. of 30% hydrogen peroxide in 100 ml. of ice water was added to form starch xanthide and coagulate the dispersion. The product was dewatered using a Buchner funnel, pulverized to pass 10 mesh, and air dried overnight.

Calcium adduct encapsulation: alkali starch was prepared by gelatinizing a mixture of 45 g. of pearl corn starch in 250 ml. of water with a solution of 5 g. of sodium hydroxide in 75 ml. of water. Twenty grams of "Sutan Plus 6.7E" was dispersed into the paste using a "Waring" blender. A solution of 10 g. of calcium chloride in 20 ml. of water was added and mixed until coagulation took place. The resultant mass was dewatered by filtration, pulverized to pass 10 mesh, and air dried overnight.

Products prepared by the above procedure were pulverized in a mortar in the presence of acetone to extract the active ingredient which was determined by gas-liquid chromatography. The ratio of safener to butylate was determined from relative peak heights and compared with this ratio in the starting "Sutan Plus 6.7E" (1:25.8). The results as reported in Table II, below, showed significantly better recovery and less safener loss in the product of the invention.

The loss of safener to the extent observed for the procedure of Example 19 may be due to its polymerization during processing, while the additional losses in the xanthide and calcium adduct procedures most likely occured during filtration.

EXAMPLE 41

A mixture of 500 g. of pregelatinized corn flour in a solution of 950 ml. of water, 50 g. of "Joy" detergent comprising an aqueous solution of anionic and nonionic surfactants, and 40 g. of ammonium hydroxide (29% ammonia) was agitated in a double planetary mixer for 10 minutes until a smooth paste formed. Two hundred grams of "Eradicane 6.7E" was thoroughly dispersed into the paste, and the paste was gelled by rapid agitation with 20 g. of boric acid.

TABLE II

| Procedure | % Active ingredient | % Recovery of butylate | % Recovery of safener |
| --- | --- | --- | --- |
| xanthide | 20.9 | 77 | 76.6 |
| calcium adduct | 20.8 | 79 | 77.0 |
| Example 19 | 22.7 | 99 | 91.2 |

The gel was coated with 200 g. of a 1:1 mixture of pregelatinized corn flour and ungelatinized pearl corn starch. The product was sieved to pass 8 mesh and air dried overnight. Yield was 920 g. containing 3.11% S, corresponding to 18.4% a.i. and 100% recovery.

It is understood that the foregoing detailed description is given merely by way of illustration and that modification and variations may be made therein without departing from the spirit and scope of the invention.

We claim:

1. A method of encapsulating a chemical biological agent comprising the steps of:
   a. preparing a solution or dispersion of a suitable chemical biological agent in a matrix-forming material comprising an aqueous paste of a gel-forming polyhydroxy polymer (PHP), wherein said paste has a solids concentration of said PHP of from about 10-40%, and wherein the relative amount of said PHP with respect to said biological agent is sufficient to entrap said agent within a matrix of said PHP;

b. reacting from a single phase at an alkaline pH said PHP with boric acid or a boric acid derivative to form a continuous insolubilized matrix gel having entrapped therein uniformly dispersed, discontinuous domains of said agent; and c. recovering free-flowing particles of said entrapped chemical biological agent.

2. A method as described in claim 1 wherein the suitable chemical biological agent is a herbicide, insecticide, fungicide, nematocide, bactericide, rodenticide, molluscicide, acaricide, larvacide, fumigant, animal repellant, insect repellant, plant growth regulator, fertilizer, pheromone, sex lure, flavor composition, or odor composition.

3. A method as described in claim 1 wherein said gel-forming PHP is selected from the group consisting of starch, carboxymethyl cellulose, dextran, xylan, and polyvinyl alcohol.

4. A method as described in claim 1 wherein said gel-forming PHP is a starch.

5. A method as described in claim 4 wherein said starch is pregelatinized prior to preparation of said solution or dispersion.

6. A method as described in claim 4 wherein said pH is sufficiently alkaline to effect gelatinization of the starch.

7. A method as described in claim 1 wherein the pH of said solution or dispersion is in the range of 7.5 to 8.5.

8. A method as described in claim 7 wherein the pH is adjusted to within said range by the addition of ammonium hydroxide to said solution or dispersion.

9. A method as described in claim 1 wherein the recovering of free-flowing particles of said entrapped chemical biological agent comprises the steps of:
   (1) breaking the gel formed in step (b) into discrete particles;
   (2) admixing the particles with a powdery coating material whereby the particles become coated with said material; and
   (3) drying the discrete coated particles.

10. A method as described in claim 9 wherein said powdery coating material is a starch or starch-containing flour.

11. A composition of matter produced by the process of claim 1.

12. A composition of matter produced by the process of claim 2.

13. A composition of matter produced by the process of claim 3.

14. A composition of matter produced by the process of claim 4.

15. A composition of matter produced by the process of claim 10.

* * * * *